(12) United States Patent
Bräcker et al.

(10) Patent No.: US 8,532,782 B2
(45) Date of Patent: Sep. 10, 2013

(54) MUSICAL FITTING OF COCHLEAR IMPLANTS

(75) Inventors: Timo Bräcker, Innsbruck (AT); Peter Schleich, Vill (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 612 days.

(21) Appl. No.: 12/730,321

(22) Filed: Mar. 24, 2010

(65) Prior Publication Data
US 2010/0249879 A1 Sep. 30, 2010

Related U.S. Application Data

(60) Provisional application No. 61/162,758, filed on Mar. 24, 2009.

(51) Int. Cl.
*A61N 1/00* (2006.01)

(52) U.S. Cl.
USPC .......................................................... 607/57

(58) Field of Classification Search
USPC ..................................... 607/57, 56
See application file for complete search history.

(56) References Cited

U.S. PATENT DOCUMENTS

| | | | |
|---|---|---|---|
| 4,284,856 A * | 8/1981 | Hochmair et al. | 607/9 |
| 4,515,158 A | 5/1985 | Patrick et al. | 128/419 R |
| 4,711,243 A * | 12/1987 | Schafer | 607/57 |
| 5,601,617 A | 2/1997 | Loeb et al. | 607/56 |
| 5,749,912 A | 5/1998 | Zhang et al. | 607/57 |
| 5,938,691 A | 8/1999 | Schulman et al. | 607/57 |
| 6,175,767 B1 | 1/2001 | Doyle, Sr. | 607/57 |
| 6,219,580 B1 | 4/2001 | Faltys et al. | 607/57 |

(Continued)

FOREIGN PATENT DOCUMENTS

| WO | WO 99/35882 | 7/1999 |
|---|---|---|
| WO | WO 99/49815 | 10/1999 |

(Continued)

OTHER PUBLICATIONS

Kral, A., et al, "Spatial resolution of cochlear implants: the electrical field and excitation of auditory afferents", *Hearing Research*, vol. 121 (1998, pp. 11-28.
Loizou, P.C., "Signal Processing for Cochlear Prosthesis: A Tutorial Review", *IEEE*, Jan. 1997, pp. 881-885; 0-7803-3694-1/97.
Loizou, P.C., "Signal-Processing Techniques for Cochlear Implants", *IEEE Engineering in Medicine and Biology*, May/Jun. 1999, pp. 34-46.

(Continued)

*Primary Examiner* — Niketa Patel
*Assistant Examiner* — Alyssa M Alter
(74) *Attorney, Agent, or Firm* — Sunstein Kann Murphy & Timbers LLP

(57) ABSTRACT

A method of developing a weighting matrix for a cochlear implant patient is described. An electrode stimulus signal is derived from a first musical signal. A set of further stimulus signals is derived that have a defined musical relation to the first musical signal. A set of weighting values are selected for the stimulation electrodes for the electrode stimulus signal. Then the weighting values are set for the stimulation electrodes for each of the further stimulus signals. Each of the stimulus signals is consecutively presented to the patient and the weighting values individually adjusted for each of the further stimulus signals until the series of stimulus signals elicits an increasing pitch percept according to the defined musical relation. The adjusted weighting values are stored and assigned to a corresponding analysis channel. The process is iteratively repeated using one of the further stimulus signals as the first electrode stimulus signal until weighting values for a complete frequency range have been derived.

9 Claims, 4 Drawing Sheets

(56) References Cited

U.S. PATENT DOCUMENTS

| | | |
|---|---|---|
| 6,289,247 B1 | 9/2001 | Faltys et al. ............... 607/57 |
| 6,295,472 B1 | 9/2001 | Rubinstein et al. .......... 607/55 |
| 6,584,525 B1 | 6/2003 | Klingman ................... 710/118 |
| 6,594,525 B1 | 7/2003 | Zierhofer ................... 607/57 |
| 6,600,955 B1 | 7/2003 | Zierhofer ................... 607/57 |
| 6,778,858 B1 | 8/2004 | Peeters ..................... 607/57 |
| 6,826,430 B2 | 11/2004 | Faltys et al. ............... 607/137 |
| 7,209,789 B2 | 4/2007 | Zierhofer ................... 607/57 |
| 2001/0031909 A1 | 10/2001 | Faltys et al. ............... 600/25 |
| 2004/0082985 A1 | 4/2004 | Faltys et al. ............... 607/116 |
| 2005/0107843 A1 | 5/2005 | McDermott et al. ........ 607/57 |
| 2005/0203589 A1 | 9/2005 | Zierhofer ................... 607/57 |
| 2006/0052841 A1 | 3/2006 | Daly et al. ................. 607/57 |
| 2006/0080087 A1 | 4/2006 | Vandali et al. ............. 704/207 |
| 2006/0227986 A1 | 10/2006 | Swanson et al. ........... 381/312 |
| 2006/0265061 A1 | 11/2006 | Kwon et al. ............... 623/10 |
| 2007/0156202 A1 | 7/2007 | Zierhofer ................... 607/57 |
| 2007/0225776 A1 | 9/2007 | Fritsch et al. .............. 607/57 |

FOREIGN PATENT DOCUMENTS

| | | |
|---|---|---|
| WO | WO 01/19135 | 3/2001 |
| WO | WO 01/19304 | 3/2001 |
| WO | WO 2005/113064 | 12/2005 |
| WO | WO 2006/119069 | 11/2006 |

OTHER PUBLICATIONS

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

Secker-Walker, H., et al, "Time-domain analysis of auditory-nerve-fiber firing rates", *J. Acoust. Soc. Am.* 88(3), pp. 1427-1436 (1990).

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Wilson, B. S., et al, "Temporal Representations With Cochlear Implants", *The American Journal of Otology*, 18:530-534, 1997.

Ziese, M., et al, "Speech Understanding with the CIS and the n-of-m Strategy in the MED-EL COMBI 40+ System", *ORL*, 2000;62:321-329.

\* cited by examiner

MUSICAL FITTING OF COCHLEAR IMPLANTS

This application claims priority from U.S. Provisional Patent Application 61/162,758, filed Mar. 24, 2009, incorporated herein by reference.

FIELD OF THE INVENTION

The present invention relates to medical implants, and more specifically to fit customization in cochlear implant systems.

BACKGROUND ART

In current cochlear implant (CI) pulsatile coding strategies, the acoustic signal is usually decomposed into a set of band pass signals. The number of band pass signals is often equal to the number of electrodes contacts in the system. Thus relatively broad band passes have to be used to cover the entire acoustic frequency range transmitted by the system. With current CI systems, users already enjoy good speech understanding in silent and tolerably noisy conditions, but musical perception remains relatively unsatisfying. That may be because some musical characteristics such as frequency harmonics are not be perceived by current CI users.

For many musical instruments, the fundamental frequency (which particularly describes the pitch perception in the auditory system) is located between 100 Hz and 400 Hz. Transmission of the fundamental frequency and its first order higher harmonics is not yet accomplished in current CI systems. To adequately improve the perception of chords for CI users, the transmission of music harmonics should be advanced so that single harmonics can be represented on the basilar membrane according to their pitch.

In current CI systems, the filter band widths are usually greater than 100 Hz such that more than one harmonic is processed by each filter band. In current fine structure coding strategies, the stimulation timing is derived from the band pass signals, in which case, when multiple harmonics fall within a given filter band, the derived stimulation timing is usually not representative of any of the harmonics but instead depends on the relative amplitudes and the frequency spacing. This means that the stimulation timing in low-to-mid frequency channels is relatively complex rather than simply coding the periodicity of the dominant harmonics; usually one harmonic dominates a filter band. In normal hearing, such a harmonic masks any neighboring harmonics and carries the information that should be transmitted tonotopically and temporally correct.

In psychoacoustic pitch testing both concepts, periodic pitch and tonotopic pitch have been demonstrated to work in CI patients. To be more precise, a gradual shift of stimulation from an apical electrode towards a more basal one at relatively high rates leads to an increase in pitch percept. Nobbe et al. (Acta Oto-Laryngologica, 2007; 127:1266-1272) showed that both, simultaneous or sequential stimulation lead to just noticeable pitch changes of down to one semitone. Similar results can be found if the low stimulation rate of one electrode is increased. Pitch JNDs range down to below one semitone. These results suggest that a combination of both cues could lead to an even improved pitch perception in CI users.

One coding strategy that partially addresses the above is the Fine Structure Processing (FSP) strategy used in the Med-E1 OPUS 1 and OPUS 2 speech processors. The FSP strategy codes very low frequency harmonics, usually the fundamental frequency and the second harmonic, by using a filter bank that ranges down to below the expected fundamental frequencies. The spacing of the lowest frequency bands is such that the harmonics coded are usually resolved, that is, only one harmonic falls into one low frequency filter band. But higher harmonics are not explicitly resolved by this type of signal processing. In addition, the shift of harmonics is mainly coded temporally. A tonotopic shift of the temporal code of fundamental frequency gliding from 100 Hz up is only achieved at around 200 Hz. Explicit mapping of tonotopicity according to channel specific stimulation rates is not possible with this strategy.

The HiRes 120 strategy of Advanced Bionics Corporation uses active current steering and additional spectral bands. The input signal is filtered into a large number of spectral bands and fast Fourier transformation (FFT) algorithms are applied for fine spectral resolution. Hilbert processing derives temporal detail from the signals while the spectral maximum for each electrode pair is determined across all the filter bands. Pulse rate and stimulus location are determined from the estimated frequency of the spectral maximum. A number of spectral bands are assigned to each electrode pair and the spectral bands are delivered to locations along the electrode array by accurately varying the proportion of current delivered simultaneously to adjacent electrodes in each electrode pair. To our knowledge the strategy does not contain any means to correct the mismatch between stimulation rates derived from sub bands and tonotopicity.

Another stimulation concept was described by Kasturi K. & Loizou P., *Effect Of Filter Spacing On Melody Recognition: Acoustic And Electric Hearing*, Journal of Acoustic Society of America, 122(2), 2007, p. EL 29-EL 34; incorporated herein by reference. A semitone filter bank was used to more accurately analyze melodies. A set of 12 semitone filters was assigned to an equal number of stimulation electrodes. They divided a certain frequency range into a number of channels and analyzed the melody recognition of CI users. They pointed out, that the melodies processed with the semitone filter spacing were preferred over melodies processed by the conventional logarithmic filter spacing.

In U.S. Patent Publication 20080021551 (incorporated herein by reference) a system for optimizing pitch perception in CIs is described where a reference signal is generated and applied to an appropriate electrode on the electrode array. A probe signal having a fixed interval relationship with the reference signal is applied to an appropriate electrode on the electrode array. The location of the probe signal or reference signal is shifted until the two signals match. A frequency map is applied that uses the location at which the probe signal and the location at which the reference signal is applied when the two signals match. The frequency map is used to apply stimulus signals to correct locations within a cochlea as a function of pitch.

SUMMARY OF THE INVENTION

Embodiments of the present invention are directed to a method of developing a weighting matrix for a cochlear implant patient. An electrode stimulus signal is derived from a first musical signal. A set of further stimulus signals is derived that have a defined musical relation to the first musical signal. A set of weighting values are selected for the stimulation electrodes for the electrode stimulus signal. Then the weighting values are set for the stimulation electrodes for each of the further stimulus signals. Each of the stimulus signals is consecutively presented to the patient and the weighting values individually adjusted for each of the further stimulus signals until the series of stimulus signals elicits an increasing pitch percept according to the defined musical relation. The adjusted weighting values are stored and assigned to a corresponding analysis channel. The process is iteratively repeated using one of the further stimulus signals as the first electrode stimulus signal until weighting values for a complete frequency range have been derived.

In some embodiments, unobserved weighting values may be interpolated. The first musical signal may be a musical note. The defined musical relation may be based on a musical melody known to the patient. The electrode stimulus signal may be based on a lowest pitch percept for the patient, and may be based on deriving temporal fine structure from multiple band pass signals—for example, from a semitone filter bank—and, the number of band pass signals may be much greater than the number of stimulation electrodes. The electrode stimulus signals may be delivered simultaneously to the stimulation electrodes.

Embodiments of the present invention also include a method of generating electrode stimulation signals for an implanted electrode array. An acoustic audio signal is processed to generate multiple band pass signals, each of which represents an associated band of audio frequencies. Stimulation information is extracted from the band pass signals to generate a set of stimulation event signals that define the electrode stimulation signals. The stimulation event signals are weighted with a weighting matrix that reflects music perception iterative fit data to produce a set of electrode stimulation signals. The electrode stimulation signals are developed into a set of output electrode pulses to the electrodes in the implanted electrode array.

DETAILED DESCRIPTION OF SPECIFIC EMBODIMENTS

Various embodiments of the present invention are directed to a new coding and fitting algorithm suited for the transmission of music characteristics, especially harmonics. Musical intervals are individually mapped to stimulation sites along a cochlear implant electrode. Musical intervals smaller than an octave down to semitones can be assigned to individual weighting of simultaneously activated electrodes. This mapping provides for individualized imaging harmonic characteristics for specific cochlear implant users to improve music perception and enjoyment with a cochlear implant.

Figure 1:
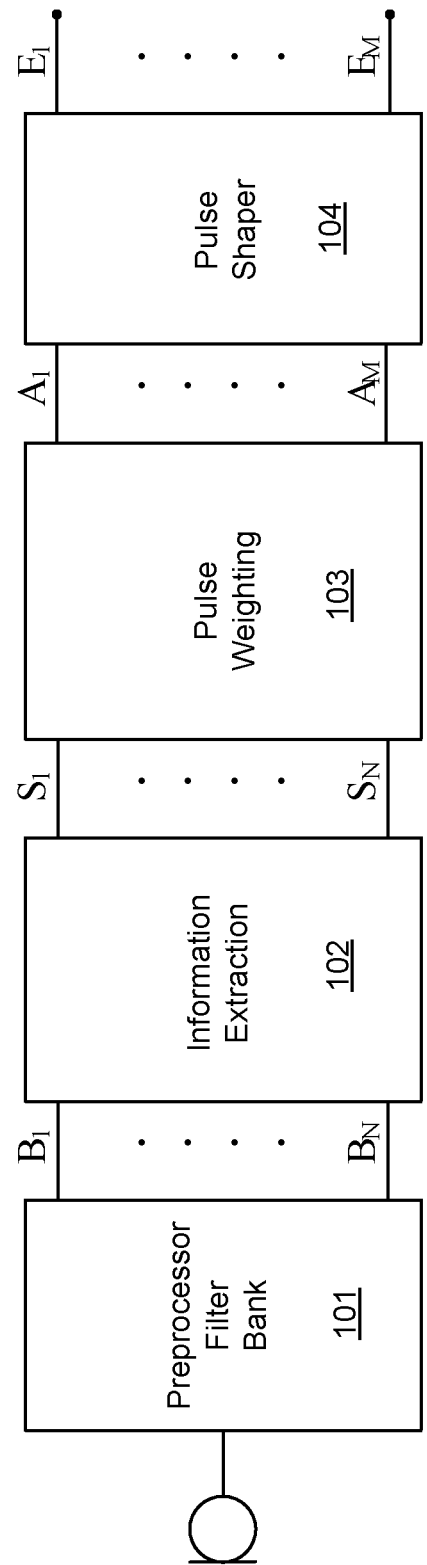
FIG. 1 shows functional signal processing blocks according to one specific embodiment of the present invention.
Figure 2:
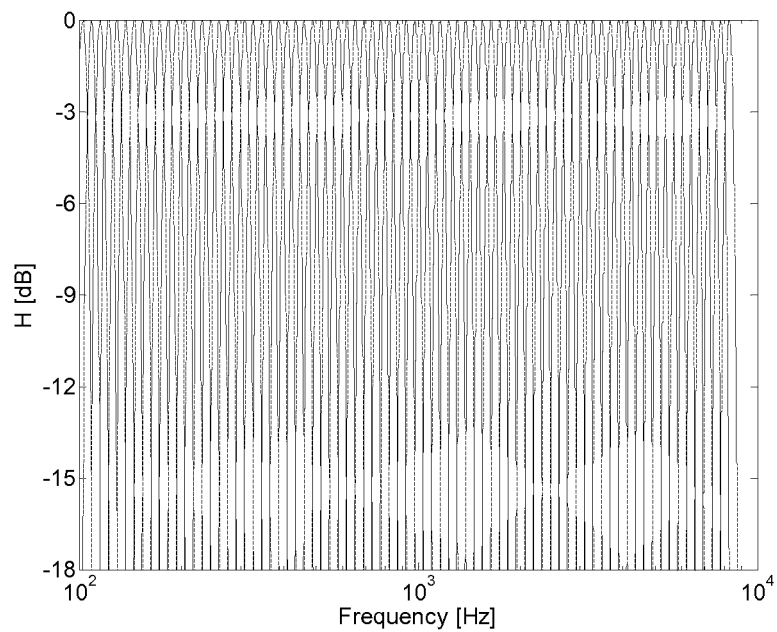
FIG. 2 shows an example of the frequency response of a filter bank capable of distinguishing all the semitones.

FIG. 1 shows functional signal processing blocks according to one specific embodiment of the present invention wherein some relatively large number N band pass signals containing stimulation timing and amplitude information are assigned to a smaller number M stimulation electrodes. Preprocessor Filter Bank 101 pre-processes an initial acoustic audio signal, e.g., automatic gain control, noise reduction, etc. Each band pass filter in the Preprocessor Filter Bank 101 is associated with a specific band of audio frequencies so that the acoustic audio signal is filtered into some N band pass signals, $B_1$ to $B_N$ where each signal corresponds to the band of frequencies for one of the band pass filters. Preferably, the filter bank has a high number of narrow frequency band filters for differentiating and mapping the analyzed frequency range. FIG. 2 shows an example of the frequency response of a filter bank capable of distinguishing all the semitones. In one specific embodiment, a frequency range from 100 Hz to 8.5 kHz, is analyzed using 77 filter bands each having a bandwidth of one semitone.

The band pass signals are input to an Information Extractor 102 which extracts signal specific stimulation information—e.g., envelope information, phase information, timing of requested stimulation events, etc.—into a set of N stimulation event signals $S_1$ to $S_N$, which represent electrode specific requested stimulation events. For example, channel specific sampling sequences (CSSS) may be used as described in U.S. Pat. No. 6,594,525, which is incorporated herein by reference. The band pass signals are pooled into a smaller number of overlapping macro bands, and within each macro band the channel with the highest envelope is selected for a given sampling interval. The stimulation events are decimated based on channel interaction and inhibition functions to extract the temporal fine structure of the band pass signals.

Pulse Weighting 103 weights each requested stimulation event signal $S_1$ to $S_N$ with a weighted matrix of stimulation amplitudes that reflect patient-specific perceptual characteristics to produce a set of electrode stimulation signals $A_1$ to $A_M$ that provide and optimal electric tonotopic representation of the acoustic signal. Matrix weighting of the stimulation pulses is described further in U.S. Patent Application 61/046,832, filed Apr. 22, 2008, which is incorporated herein by reference. Equation 1 shows a typical weighting matrix of size M×N:

$$W = \begin{pmatrix} 1 & 0.923 & 0.846 & \ldots & \ldots & 0 & 0 & 0 \\ 0 & 0.077 & 0.154 & \ldots & \ldots & 0 & 0 & 0 \\ 0 & 0 & 0 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.154 & 0.077 & 0 \\ 0 & 0 & 0 & \ldots & \ldots & 0.846 & 0.923 & 1 \end{pmatrix} \quad \text{Equation 1}$$

where M is the number of independently addressable stimulation electrodes, and N is the number of analysis filter bands. A negative weighting factor $W_{ij}$ indicates an inverted electrical pulse.

Figure 6:
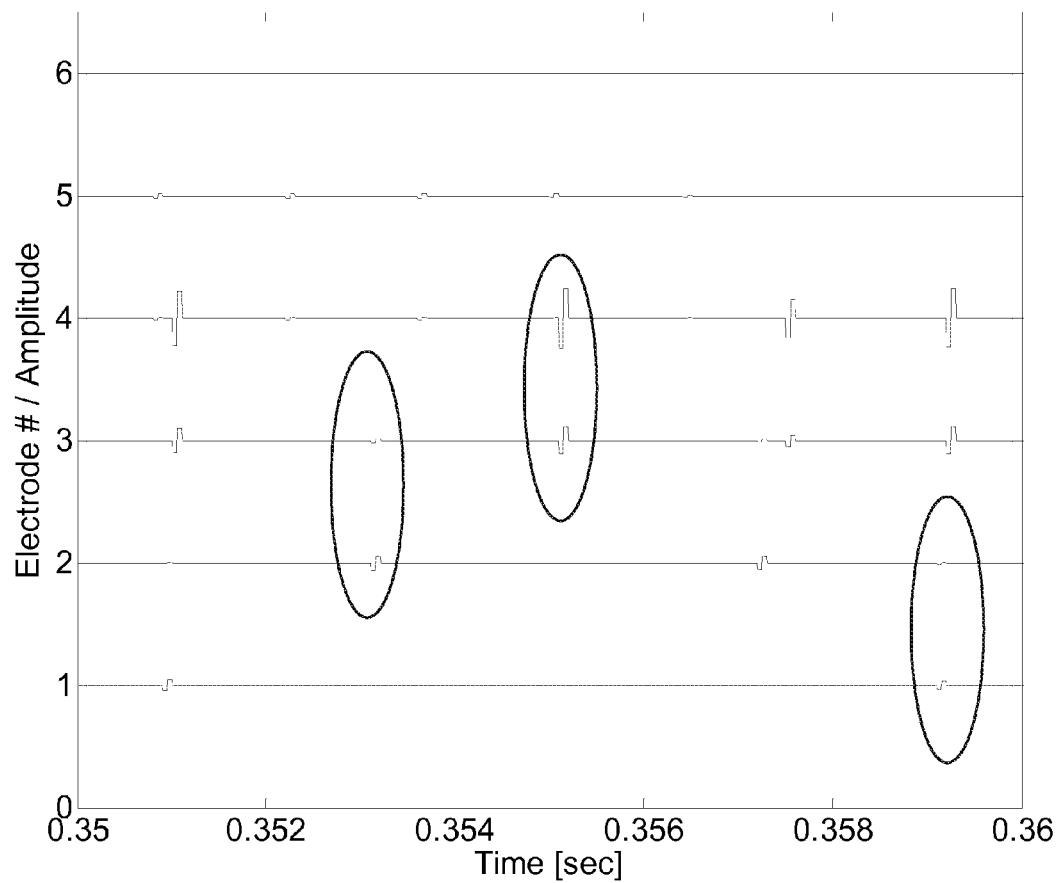
FIG. 6 shows details of simultaneous stimulation pulses.

Finally, patient specific stimulation is achieved by individual amplitude mapping and pulse shape definition in Pulse Shaper 104 which develops the set of electrode stimulation signals $A_1$ to $A_M$ into a set of output electrode pulses $E_1$ to $E_M$ to the electrodes in the implanted electrode array which stimulate the adjacent nerve tissue. FIG. 6 shows details of simultaneous stimulation pulses. Whenever one of the requested stimulation event signals $S_1$ to $S_N$ requests a stimulation event, the respective number of electrodes is activated with a set of output electrode pulses $E_1$ to $E_M$. This fitting scheme can be used to individually adjust the mapping of analysis bands to stimulation sites along the cochlea.

Figure 3:
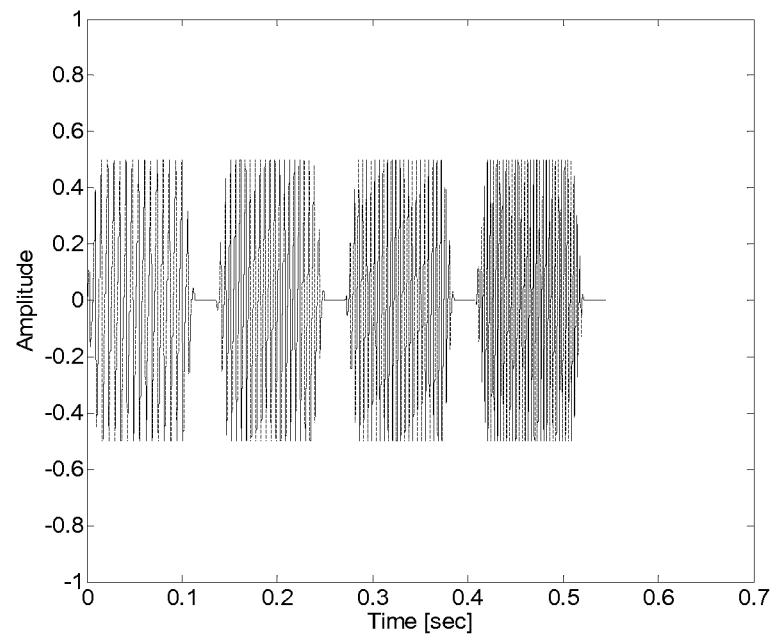
FIG. 3 shows a synthesized musical fanfare having several harmonics.
Figure 4:
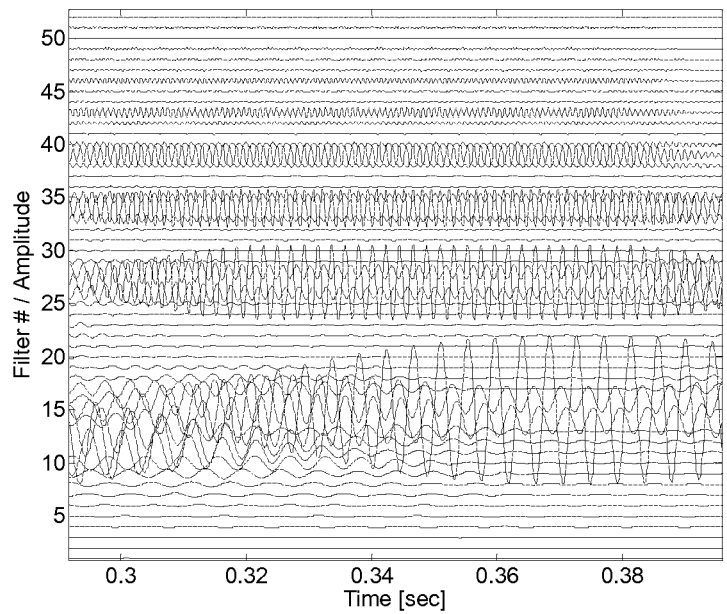
FIG. 4 shows the resulting band pass signals generated by a semitone filter bank.
Figure 5:
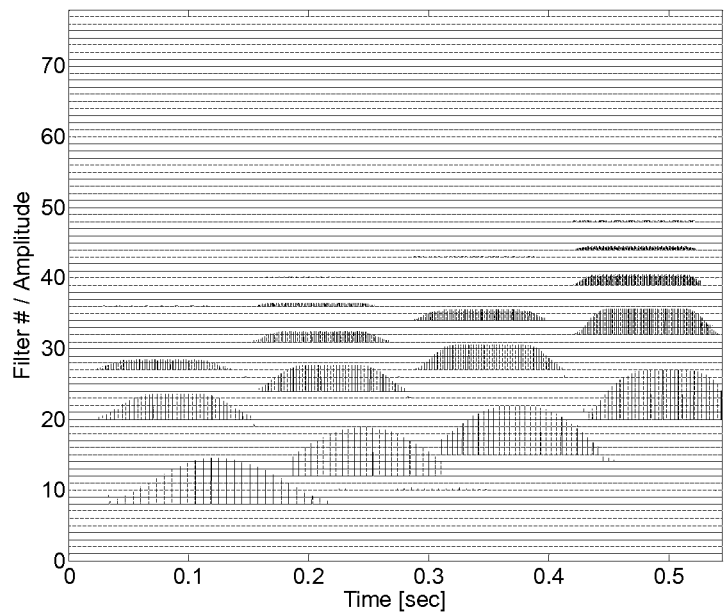
FIG. 5 shows time events that would be selected on channels containing dominant harmonic information.

A fit method for such a cochlear implant system using the idea of filter assignment as described above may be used to code musical intervals correctly for music perception by the cochlear implant patient. One specific embodiment starts the adjustment for musical fit by initially deriving an electrode stimulus signal from a first musical signal such as a musical note. A set of further stimulus signals also is derived that have a defined musical relation to the first musical signal; e.g., musical notes which are in a defined musical relation to the first musical note (major third, perfect fifth, perfect octave . . . ). These selections may be usefully based on musical intervals according to melodies that the cochlear implant patient knows well. FIG. 3 shows a synthesized musical fanfare having several harmonics. FIG. 4 shows the resulting band pass signals generated by a semitone filter bank. FIG. 5 shows time events that would be selected on channels containing dominant harmonic information.

A set of weighting values are selected for the stimulation electrodes for the electrode stimulus signal; for example, based on previously fitted musical notes. In the first iteration, the electrode eliciting the lowest pitch percept may be selected. Then the weighting values are set for the stimulation electrodes for each of the further stimulus signals. Each of the stimulus signals is consecutively presented to the patient and the weighting values individually adjusted for each of the further stimulus signals until the series of stimulus signals elicits an increasing pitch percept according to the defined musical relation. The adjusted weighting values are stored and assigned to a corresponding analysis channel. The process is iteratively repeated using one of the further stimulus signals as the first electrode stimulus signal until weighting values for a complete frequency range have been derived. Any blank columns of the weighting matrix may be interpolated. A more detailed description of the fitting method applied to a specific implementation of a cochlear implant system follows.

A specific embodiment may start the musical fitting process with a filter assigned to the musical note A (110 Hz). First, the stimulation electrode eliciting the lowest pitch (usually the most apical one) will be individually stimulated with a fundamental pulse rate (e.g. 110 pps according to the musical note A). The musical note A then is assigned to the analysis filter band 1. So in a cochlear implant system that synchronizes or derives stimulation events to (for example) zero crossings in a band pass signal, the stimulation signal of filter band 1 then would correspond to a stimulation rate of 110 pps. The stimulation pulses are assigned to the most apical electrode E1.

110 Hz→filter band 1→110 pps→1*E1+0*E2+0*E3+ . . . +0*E12 (e.g.)

Equation 2 shows the weighting matrix used for stimulation of the first stimulus:

$$W = \begin{pmatrix} 1 & 0 & 0 & 0 & 0 & \ldots & 0 & 0 \\ 0 & 0 & 0 & 0 & 0 & \ldots & 0 & 0 \\ 0 & 0 & 0 & 0 & 0 & \ldots & 0 & 0 \\ \ldots & \ldots & \ldots & \ldots & \ldots & \ldots & \ldots & \ldots \\ 0 & 0 & 0 & 0 & 0 & \ldots & 0 & 0 \\ 0 & 0 & 0 & 0 & 0 & \ldots & 0 & 0 \end{pmatrix} \quad \text{Equation 2}$$

Then a second stimulus is presented, for example, 138.6 pps according to a major third of the first musical note. The cochlear implant user adjusts the pitch of the second stimulus, so that it sounds like the intended harmonic interval (e.g. major third) in relation to the pitch of the first stimulus. This adjustment is achieved by shifting simultaneous stimulation between activated electrodes.

138 Hz→filter band 5→138 pps→0.2*E1+0.8*E2+0*E3+ . . . +0*E12

The adjustment of a first musical interval results in an adjusted weighting matrix containing new weighting factors, e.g.:

$$W = \begin{pmatrix} 1 & 0 & 0 & 0 & 0.2 & \ldots & 0 & 0 \\ 0 & 0 & 0 & 0 & 0.8 & \ldots & 0 & 0 \\ 0 & 0 & 0 & 0 & 0 & \ldots & 0 & 0 \\ \ldots & \ldots & \ldots & \ldots & \ldots & \ldots & \ldots & \ldots \\ 0 & 0 & 0 & 0 & 0 & \ldots & 0 & 0 \\ 0 & 0 & 0 & 0 & 0 & \ldots & 0 & 0 \end{pmatrix} \quad \text{Equation 3}$$

Since the adjusted stimulus is based on a major third interval of the first musical note (four semitones above the first note), column 5 which is assigned to the fifth analysis channel now contains weighting factors. This method can be performed with one or more intervals that are subjectively adjusted per iteration.

In the next iteration, the musical note serving as the prime or fundamental is selected from the set of intervals used in the previous adjustment, for example, 138 Hz. As measured in the previous iteration, a stimulus with 138 pps is simultaneously applied to 0.2*E1+0.8*E2. The second note for this iteration could again be a major third (174 Hz).

174 Hz→filter band 9→174 pps→0*E1+0.6*E2+0.4*E3+ . . . +0*E12 (e.g.)

After a certain number of iterations, the weighting matrix will still contain empty columns according to musical notes that have not been tested. These gaps can be interpolated from the values of the neighboring non-empty cells. Finally, every semitone of the frequency range of the analysis filter bank is mapped to one specific weighted code of simultaneously active electrodes.

Musical fitting as described above allows more exact individual tonotopic adjustment for cochlear implant users. Musical intervals and even musical chords may be perceived more naturally than in the past. In cochlear implant systems which address the temporal fine structure as well as the spectrum, a mismatch between the percepts of the two properties of tonotopicity and periodicity can occur by standard straight-forward assigning of filter bands to stimulation electrodes. That issue has not been addressed in previous cochlear implant fitting procedures. In cochlear implant systems which analyze the envelope of band pass signals, and therefore mainly the tonotopic structure, filter bands can be individually adjusted. Until now, filter bands were shifted on a global scale, the lowest and/or highest cut off frequency will be adjusted and corner frequencies of the analysis filters are spaced (e.g. logarithmically) in between. That approach still results in incorrect percepts of musical intervals, and embodiments as described above can also be used to fit purely spectrum/envelope based cochlear implant systems more precisely.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of developing a weighting matrix for a cochlear implant patient comprising:
    deriving an electrode stimulus signal from a first musical signal including frequency harmonics;
    deriving a set of further stimulus signals having a defined musical relation to the first musical signal;
    selecting a set of weighting values for the stimulation electrodes for the electrode stimulus signal;
    setting the weighting values for the stimulation electrodes for each of the further stimulus signals;
    consecutively presenting each of the stimulus signals to the patient and individually adjusting the weighting values for each of the further stimulus signals as a function of the frequency harmonics until the series of stimulus signals elicits an increasing pitch percept according to the defined musical relation;
    storing the adjusted weighting values and assigning them to a corresponding analysis channel;
    iteratively repeating the process using one of the further stimulus signals as the first electrode stimulus signal until weighting values for a complete frequency range have been derived so as to map musical intervals to individual stimulation electrodes.

2. A method according to claim 1, further comprising:
    interpolating unobserved weighting values.

3. A method according to claim 1, wherein the first musical signal is a musical note.

4. A method according to claim 1, wherein the defined musical relation is based on a musical melody known to the patient.

5. A method according to claim 1, wherein the electrode stimulus signal is based on a lowest pitch percept for the patient.

6. A method according to claim 1, wherein the electrode stimulus signals are delivered simultaneously to the stimulation electrodes.

7. A method according to claim 1, wherein deriving the electrode stimulus signal is based on deriving temporal fine structure from a plurality of band pass signals.

8. A method according to claim 7, wherein the band pass signals are derived from a semitone filter bank.

9. A method according to claim 7, wherein the number of band pass signals is much greater than the number of stimulation electrodes.

* * * * *